U S 0 0 5 2 4 5 0 1 6 A

United States Patent [19]
Odell et al.

[11] Patent Number: 5,245,016
[45] Date of Patent: Sep. 14, 1993

[54] PSEUDOMONAS MALTOPHILIA IMMUNOGLOBULIN BINDING PROTEIN AND METHODS FOR ITS USE

[75] Inventors: William D. Odell; Sanjeev Grover; Zeil A. McGee, all of Salt Lake City, Utah

[73] Assignee: University of Utah Research Foundation, Salt Lake City, Utah

[21] Appl. No.: 690,608

[22] Filed: Apr. 24, 1991

Related U.S. Application Data

[63] Continuation-in-part of Ser. No. 648,486, Jan. 31, 1991, abandoned.

[51] Int. Cl.$^5$ .......................... C07L 3/02; C07K 3/20; C07K 15/04
[52] U.S. Cl. ................... 530/390.5; 436/513; 530/413; 530/825
[58] Field of Search ...................... 530/412, 413, 387.1, 530/389.1, 390.1, 390.5, 825; 436/513, 536, 538, 541

[56] References Cited

U.S. PATENT DOCUMENTS

| | | | |
|---|---|---|---|
| 3,850,798 | 11/1974 | Sjöquist | 210/31 C |
| 4,490,289 | 12/1984 | Stern | 530/351 |
| 4,567,140 | 1/1986 | Voelskow et al. | 435/42 |
| 4,569,913 | 2/1986 | Koths et al. | 435/190 |
| 4,704,366 | 11/1987 | Juarez-Salinas et al. | 530/413 |
| 4,757,135 | 7/1988 | Schwaiger | 534/618 |
| 4,801,687 | 1/1989 | Ngo | 530/387 |
| 4,826,602 | 5/1989 | Revis et al. | 210/611 |
| 4,876,194 | 10/1989 | Björck et al. | 435/68 |

FOREIGN PATENT DOCUMENTS

| | | |
|---|---|---|
| 0282308 | 3/1988 | European Pat. Off. |
| 0284368 | 3/1988 | European Pat. Off. |

OTHER PUBLICATIONS

The Proteins, 3rd ed. Neurath et al., ed. Academic Press, Published 1975, vol. 1, pp. 187-188.
Clinical Research, 38:173A, Jan. 1990, "An Immunoglobulin Binding Protein From Pseudomonas maltophilia", S. Grover et al.
2-Hormone Pharmacol, 86:150778z, 1977, "Specific gonadotropin binding to Pseudomonas maltophilia", Nancy D. Richert et al.
Chemical Abstracts, 111:74553q, 1989, "Demonstration and partial characterization of ADP-ribosylation in Pseudomonas maltophilia".
Chemical Abstracts, 110:227522k, 1989, "A peptidyl dipeptidase-4 from Pseudomonas maltophilia: purification and properties".
10-Microbial Biochem., 110:91745a, 1989, "Immunoelectron microscopic demonstration of an esterase on the outer membrane of Xanthomouas maltophilia".
9-Biochem. Methods, 110:91575v, 1989, "Reconstitution of Pseudomonas maltophilia HOG receptor to liposomes by dialysis method".
Chemical Abstracts, 108:201185m, "A study of extraction of HOG binding substances from Pseudomonas maltophilia".

(List continued on next page.)

Primary Examiner—Jeffrey E. Russel
Attorney, Agent, or Firm—Madson & Metcalf

[57] ABSTRACT

A protein isolated from Pseudomonas maltophilia is found to possess an exposed, immunologically accessible protein which binds to the FC region of several species of immunoglobulins. The protein is found to bind both IgG and IgA immunoglobulins and is found to have an effective molecular weight of approximately 30,000 daltons. The protein is found to be useful in isolation of IgA immunoglobulins from biological mixtures. The protein makes IgA immunoglobulins available for further analytical techniques, including identifying bacteria which contain IgA binding proteins. Because of the increased availability of IgA immunoglobulins, it is possible to diagnosis and treat IgA-related diseases and their sources.

18 Claims, 10 Drawing Sheets

OTHER PUBLICATIONS

10–Microbial Biochem., 108:109293x, 1988, "A study on the specific human chorionic gonadotropin (HOG) binding to *Pseudomonas maltophilia*".

Falkenberg et al. "Purification of Streptococcal Protein G Expressed by *Escherichia coli* by High Performance Liquid Affinity Chromatography Using Immobilized Immunoglobulin G and Albumin", Biochemical Chromatography 2:221/225 (1987).

Jungbauer et al. "Comparison of Protein A, Protein G and Copolymerized Hydroxyapatite for the Purification of Human Monoclonal Antibodies", Journal of Chromatography, 476:257–268 (1989).

Haun, et al. "A rapid procedure for the purification of IgA$_1$ and IgA$_2$ subclasses from normal human serum using protein G and jackfruit lectin (jacalin) affinity chromatography", Immunology Letters, 22:273–279 (1989).

"Protein A of *Staphylococcus aureus* and Related Immunoglobulin Receptors Produced by Streptococci and Pheumonococci", John J. Langone, *Advances in Immunology*, vol. 32, pages 158 through 243. 1982.

"Protein A Isolated from *Staphylococcus aureau* after Digestion with Lysostaphin", John Sjöquist, Bedrich Meloun, and Hans Jhelm, *Eur. J. Biochem.*, 29, 572–578 (1972).

"Protein L. A. Novel Bacterial Cell Wall Protein with Affinity for Ig L Chains[1]", Lars Björck, *The journal of Immunology*, vol. 140, No. 4, pages 1194 through 1197. (1988).

"Nonimmune Binding of Ig TO *Clostridium perfringens* Preferential Binding of IgM and Aggregated IgG[1]", Gunnar Lindahl and Böran Kronvall, *The Journal of Immunology*, vol. 140, No. 4, Feb. 15, 1988, pages 1223 through 1227.

"Isolation and Characterization of a 14–kDa Albumin-binding Fragment of Stretpococcal Protein G[1]", Ulf Sjöbring, Cecelia Falkenberg, Egon Nielsen, Bo Åkerström, and Lars Björck, *The Journal of Immunology*, vol. 140, No. 5, Mar. 1, 1988, pages 1595 through 1599.

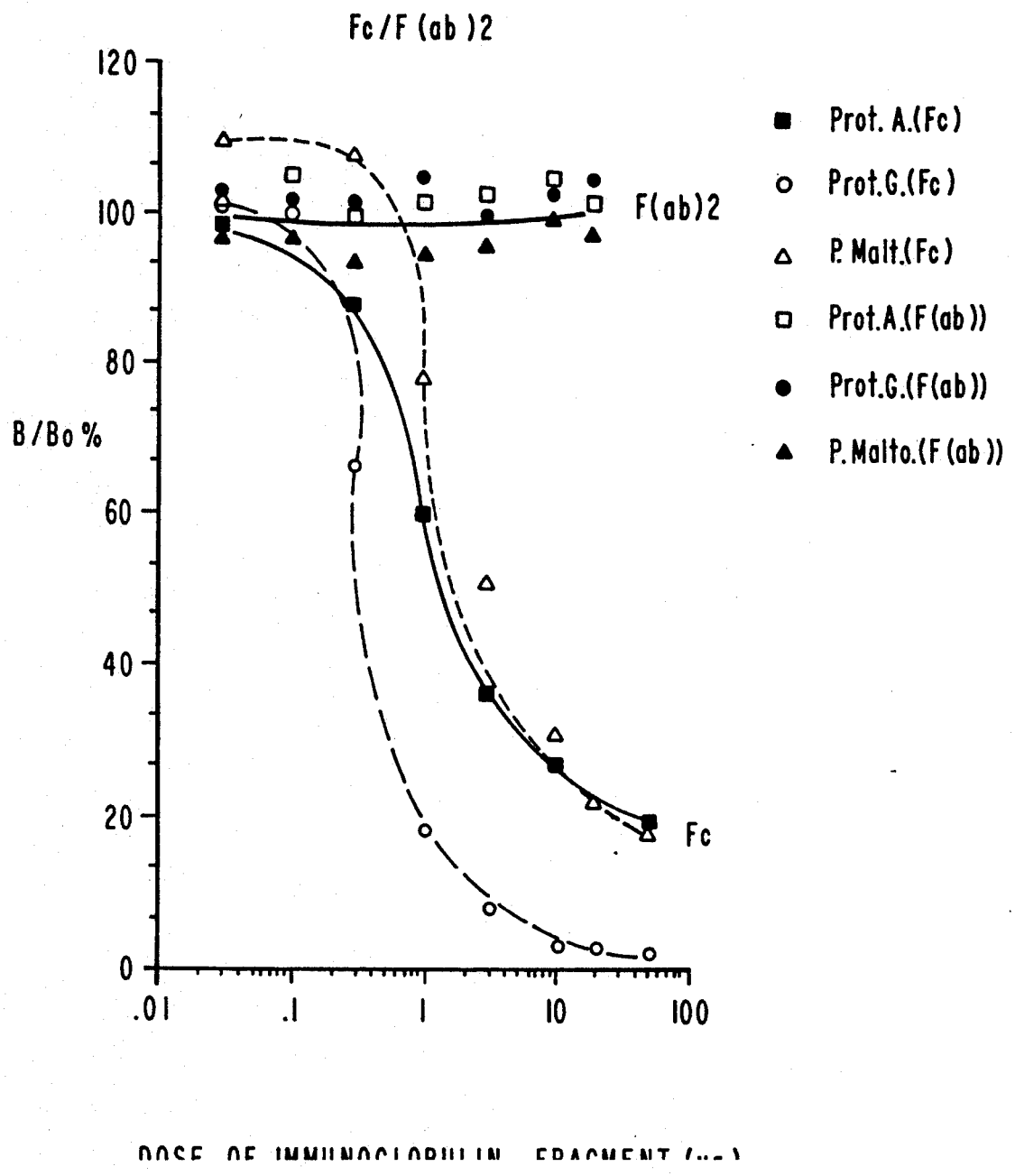

PSEUDOMONAS MALTOPHILIA IMMUNOGLOBULIN BINDING PROTEIN AND METHODS FOR ITS USE

This invention was made with government support under Grant No. R01-HD18986-04 awarded by the Department of Health and Human Services/Institutes of Health. The government has certain rights in the invention.

RELATED APPLICATIONS

This application is a continuation-in-part application of applicants' copending U.S. Pat. application Ser. No. 07/648,486, filed Jan. 31, 1991, now abandoned, entitled "Immunoglobulin Binding Protein From Pseudomonas Maltophilia and Methods For Its Use," which is incorporated herein by this reference.

BACKGROUND 1. The Field of the Invention

The present invention is related to a protein isolated from the cell wall of the bacterium *Pseudomonas maltophilia* and having the ability to bind IgA immunoglobulins, as well as IgG immunoglobulins, said protein having a molecular weight of approximately 30,000 daltons. The present invention is further related to the use of said protein in the isolation and purification of IgA immunoglobulins, and the isolation and purification of bacteria having specific desired characteristics.

2. Technical Background

In the art a number of immunoglobulin binding proteins are known and widely used. In particular, a number of such proteins are known which are capable of binding the Fc region of IgG immunoglobulins. For example, various strains of *Staphylococcus aureus* carry a Type I receptor, commonly known as Protein A. Protein A is known to bind the Fc region of IgG. As would be expected, the ability of Protein A to bind IgG at its Fc region has made it an important immunological tool. For example, the binding characteristics of Protein A allow it to be employed in separating IgG immunoglobulins from other materials, and in diagnosing conditions involving abnormal levels of IgG immunoglobulins.

Other materials are also known to have immunoglobulin binding properties. Certain strains of Groups A, C, and G of streptococci possess a Type II receptor on their surface which also binds the Fc region of IgG. A receptor on Groups C and G Streptococci has been reported which binds the F(ab¹)₂ region of IgG. Thus, it can be seen that a number of immunoglobulin binding proteins have been identified and used.

In addition to the conventional immunoglobulin binding proteins mentioned above, the existence of binding proteins which bind to regions outside the Fc region have also been reported, and are now known in the art. There exist, for example, bacterial cell-wall proteins which bind large fractions of polyclonal IgM, with affinity for IgG light chains, as well as binding of kappa and lambda light chains to Group A Streptococci. Thus, workers in the art continue to identify, substances which bind one or more immunoglobulins at a specific region.

One problem that has been encountered is the lack of satisfactory immunoglobulin binding proteins which are capable of specifically binding IgA immunoglobulins. While some IgA binding materials have now been reported, the effectiveness of these materials in actual laboratory and clinical practice has been limited. At the same time, binding materials which are typically useable in the laboratory or clinic have not bound IgA. For example, the widely used and accepted Proteins A and G bind IgG immunoglobulins but are not known to bind IgA.

The lack of suitable IgA binding materials renders difficult the production of pure IgA immunoglobulins. Without an acceptable IgA binding protein it is not practical to produce IgA from a mixture of biological fluids. IgA is instead produced from a myeloma cell line (available from the American Type Culture Collection, Rockville, Md.) which produces murine monoclonal IgA antibody to trinitrophenol.

The IgA produced from this cell line then requires further processing and purification to remove impurities. This process is complex and expensive and requires additional purification procedures prior to use of the collected product. One of the results of these problems is that IgA immunoglobulins are scarce and their use in research and in medicine is correspondingly limited. The production of pure IgA is also extremely expensive, requiring the steps of producing the monoclonal product and the additional purification steps.

The lack of readily available IgA binding proteins has made it difficult to conduct studies of the presence, characteristics, and effects of IgA immunoglobulins. For example, certain diseases are known to be accompanied by abnormal levels of IgA immunoglobulins. Such diseases include IgA-related myeloma, certain gastrointestinal diseases, and some kidney diseases. It would be helpful to be able to easily and readily quantify IgA in order to aid in diagnosis of these abnormalities. With present purification techniques for IgA, however, such diagnosis is necessarily limited in scope.

It would certainly be of interest to further study the causes of the diseases mentioned above, but the limited availability of IgA and IgA binding materials limits this work. It would also be of interest for research and diagnostic purposes to isolate IgA containing bacteria and to separate those bacteria from other bacteria. Clearly, an effective and useable IgA binding material would facilitate this procedure.

Accordingly, it would be an advancement in the art to provide a material which readily bound IgA immunoglobulins. It would be another advantage to provide such a material which could be readily and easily used in the purification of IgA, thus avoiding the complex and expensive IgA isolation procedures presently in use.

It would be a related advancement in the art to provide a simple and easily operable method for isolating IgA immunoglobulins from a wide variety of biological fluids. It would also be an advancement in the art to provide a mechanism for separating bacteria containing IgA immunoglobulins from bacteria lacking IgA immunoglobulins. It would be a further advancement in the art to provide diagnostic and research means for quantifying IgA in disease mechanisms and in studying IgA-related illnesses.

The such methods and compositions are disclosed and claimed herein.

BRIEF SUMMARY AND OBJECTS OF THE INVENTION

The present invention is related to a protein isolated from the cell wall of the bacterium *Pseudomonas maltophilia* and having the ability to bind IgA immunoglobulins, as well as IgG immunoglobulins. The protein of the present invention was isolated from the cell wall of *Pseudomonas maltophilia* (ATCC 13637). By employing the teachings of the present invention, however, other IgA binding proteins from other strains of bacteria may also be isolated.

Pseudomonas Maltophilia was deposited with the American Type Culture Collection (ATCC), Rockville, Md., on Sep. 24, 1959 and was assigned the identification number ATCC 13637. That deposit has been freely available to the scientific community since the date of deposit. The deposit will be maintained by ATCC until at least the year 2022, or five years after the date of the most recent request for a sample, whichever is later.

One protein isolated from *Pseudomonas maltophilia* pursuant to the present invention has been found to have a molecular weight of approximately 30,000 daltons and is found to bind immunoglobulins in their Fc regions. The protein differs from Protein A and Protein G in that it is capable of binding the Fc region of both IgG and IgA immunoglobulins. As discussed above, most known and conventionally used immunoglobulin binding proteins bind only IgG in its Fc region.

The present invention is further related to the use of this protein in the isolation and purification of IgA immunoglobulins, and in the isolation and purification of bacteria having specific characteristics. Because of the ability of the protein described above to bind both IgG and IgA immunoglobulins, isolation and purification of IgA immunoglobulins and related bacteria is greatly facilitated.

In one such procedure, a biological sample containing a mixture of immunoglobulins and other materials is obtained. Such a sample can originate from any source containing adequate quantities of immunoglobulins, including blood, gastrointestinal fluids, cells, or other secretions. Since such samples will contain a mixture of immunoglobulins and other materials which are not of interest, it is necessary to separate the immunoglobulins from the mixture.

Separation of the immunoglobulins from the other fluid components may be accomplished by contacting the fluid with an effective concentration of the immunoglobulin binding protein of the present invention. Because the protein binds both IgA and IgG within the biological fluid, a mixture of immunoglobulins is recovered from the remainder of the materials present in the mixture. The recovered immunoglobulins are then separated into their component parts, including specifically IgA and IgG. The IgG immunoglobulins are removed by contacting the immunoglobulin mixture with an IgG binding Protein, such as Protein G. Since Protein G fails to bind the IgA in the sample, only IgA will remain.

The IgA recovery procedure may also be run in reverse, requiring only a limited number of steps. That is, the sample may be initially contacted with an IgG binding protein such as Protein A or Protein G. Since these proteins bind IgG but not IgA, IgG will be removed from the sample. This leaves a sample containing only IgA immunoglobulins, along with the remainder of the sample, which may be predominated by material which is not of interest in.

The *Pseudomonas maltophilia* protein of the present invention is then used to remove the remaining immunoglobulins from the sample. Those immunoglobulins will comprise only IgA, since the other immunoglobulins have been removed in the previous step. At this point in the process it is relatively simple to separate the IgA from the *Pseudomonas maltophilia* protein, leaving a substantially pure IgA product.

Thus, by employing the present invention, IgA can be easily and effectively isolated without the need to deal with IgA producing cell lines, complex purification techniques, and other complex procedures for isolating IgA. The *Pseudomonas maltophilia* protein of the present invention provides for isolation and purification of IgA through a series of simple steps, which are capable of being performed in a conventional laboratory setting.

The present invention is also available as a research and diagnostic tool. Since IgA can be easily isolated using conventional laboratory techniques, it is possible to quantify IgA levels in a patient by use of the IgA separation procedures outlined above. Thus, the presence of an IgA-related illnesses can be diagnosed, and their severity accessed. The source of the IgA-related illness may also be more easily identified.

Accordingly, it is a primary object of the present invention to provide a material which readily binds both IgG and IgA immunoglobulins.

It is another object of the present invention to provide such a material which can be readily and easily used in the purification of IgA, thus avoiding the complex and expensive IgA isolation procedures presently in use.

It is a related object of the invention to provide a simple and easily operable method for isolating IgA from a wide variety of biological fluids.

It is also an object of the present invention to provide a mechanism for separating bacteria containing IgA binding proteins from bacteria lacking IgA binding proteins.

It is a further object of the present invention to provide diagnostic and research means for quantifying and studying IgA-related illnesses.

These and other objects and advantages of the invention will become more fully apparent upon reference to the following detailed description and appended claims, and upon reference to the accompanying Figures.

BRIEF DESCRIPTION OF THE DRAWINGS

FIG. 2a is a does response curve showing binding of $^{125}$I-Fc$\gamma$ with its competitive displacement by unlabelled Fc$\gamma$ and F(ab$^1$)$_2$ with the protein of the present invention, Protein A and Protein G.

DETAILED DESCRIPTION OF THE PREFERRED EMBODIMENTS

Figure 1:
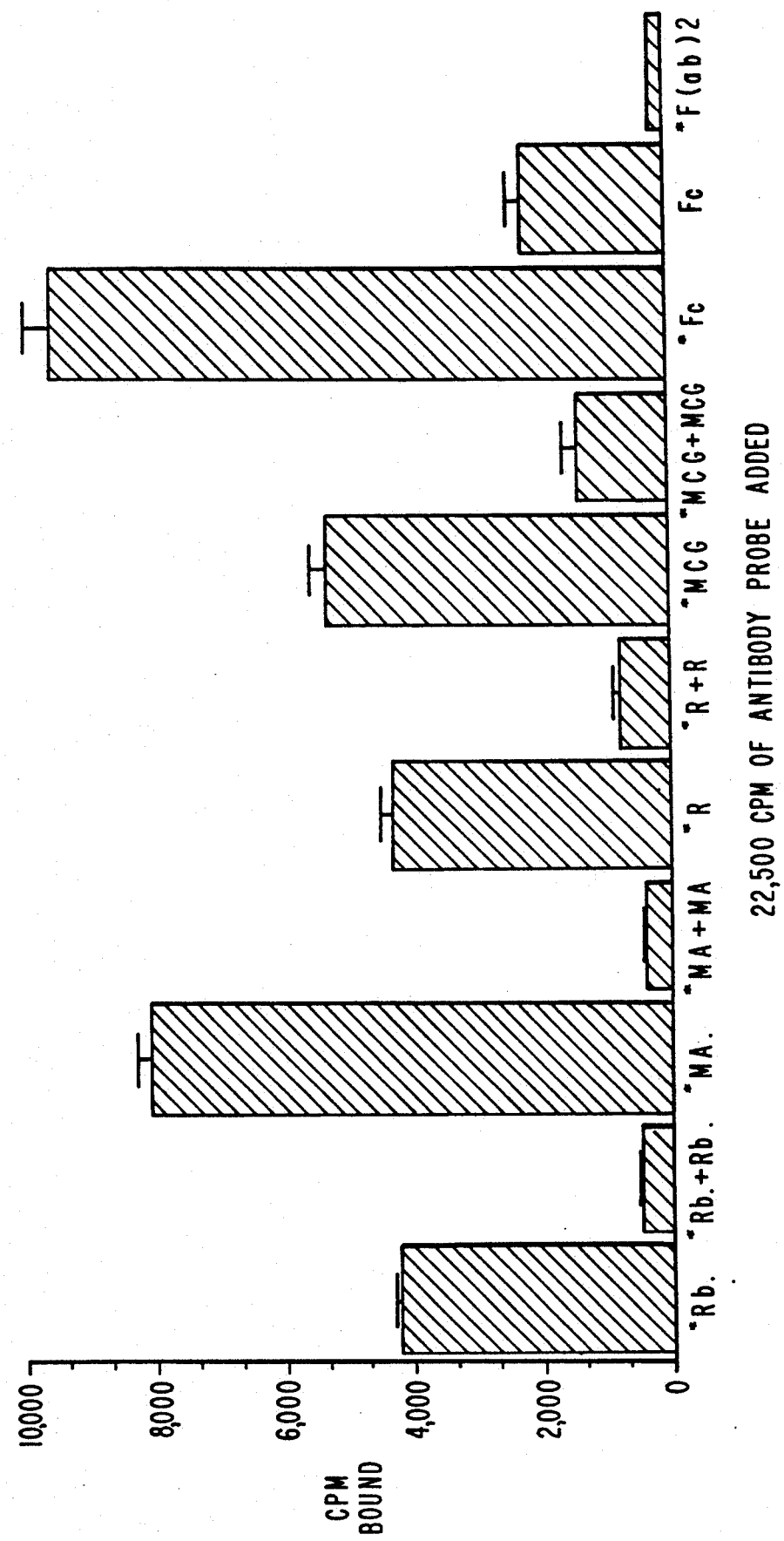
FIG. 1 is a graph which shows the binding of various $^{125}$I-immunoglobulin probes to 1.8 mg of *Pseudomonas maltophilia*, and their competitive displacement with unlabelled immunoglobulins of various species.

The present invention is related to a protein isolated from the bacterium *Pseudomonas maltophilia* (ATCC 13637) which is capable of binding the Fc region of several species of immunoglobulins. Molecular weight of the protein, as determined by SDS-PAGE and Western blot, is approximately 30,000 daltons. Of particular interest is the ability of the protein to bind both IgG and IgA immunoglobulins.

The present invention is also related to the use of the isolated 30,000 dalton protein in the isolation and purification of various type of immunoglobulins. In particular, the protein is useful in the isolation and purification of IgA because of its affinity for both IgG and IgA immunoglobulins.

The steps in the isolation procedure may, for example follow the following format. A biological sample containing a mixture of immunoglobulins and other materials is obtained. The biological sample may come from any origin as long as the sample contains necessary quantities of the immunoglobulins of interest. Such samples may, for example, originate from blood, gastrointestinal fluids, cells, or other secretions.

Next, it is necessary to separate the immunoglobulins from the mixture. This is accomplished by contacting the fluid with an effective concentration of the immunoglobulin binding protein of the present invention. Since the protein binds both IgA and IgG within the biological fluid, a mixture of immunoglobulins is recovered and separated from the remainder of the materials present in the mixture.

Finally, the isolated immunoglobulins are separated into their component parts and the IgG immunoglobulins removed. Removal of IgG may be accomplished by contacting the immunoglobulin mixture with an IgG binding Protein, such as Protein G or Protein A. Since these protein's fail to bind the IgA in the sample, only IgA will remain.

As discussed above, a procedure which is even more simple is also provided. Using this procedure the sample of biological fluid is initially contacted with an IgG binding protein such as Protein A or Protein G. By contacting the sample with this material, IgG will be removed from the sample. At this stage the sample contains only IgA immunoglobulins, along with the remainder of the sample which will be predominated by material which is not of interest in this procedure.

The *Pseudomonas maltophilia* protein of the present invention is then used to remove the remaining immunoglobulins from the sample. Those immunoglobulins will comprise only IgA, since the other immunoglobulins have been removed in the previous step. Thus, only IgA bound to the protein remains. Accordingly, it is only necessary to separate those components and remove the binding protein in order to provide IgA as a final product.

Using a similar procedure it is possible to identify bacteria which contain significant IgA binding proteins. First IgA is isolated as described above. Next the IgA is placed in position to contact one or more species of bacteria. For example, a column or gel containing IgA is prepared using methods well known in the art. Next, one or more species of bacteria are placed in contact with the IgA preparation. Since the column places the bacteria in communication with an IgA mass, only those bacteria having the capability of binding IgA are bound to the column or gel. The remainder of the materials are simply removed by known washing techniques.

By employing such a screening technique, it is possible to identify bacteria having IgA binding capabilities, and it may be possible to identify multiple IgA binding proteins such as that described herein. The present invention, therefore, opens a number of possibilities for the study of IgA and for identifying the location of IgA on the bacteria cell wall.

1. Experimental Techniques

In the identification and study of the protein of the present invention, a number of experimental techniques have been employed and are useful. These techniques, while presently preferred, are only exemplary of the techniques which could be used in the practice of the present invention.

It will also be appreciated that techniques such as those set forth below are useable in multiple experimental and clinical contexts. For example, some of these techniques may be useable, not only for identification and isolation of the proteins of interest, but also in applying the present invention in the diagnosis of disease.

Bacterial Cultures and Preparation

Multiple batches of four to six grams wet weight of *Pseudomonas maltophilia* (ATCC #13637) were grown on serum free GC agar (Difco) plus 2% vol/vol Isovitalex (BBL) at 370 C in 5% CO2, in air. The bacteria were scraped off the agar surface and weighed prior to use. Whole bacteria were suspended in 0.01M phosphate, .1S M NaCl, pH 7.4 buffer (PBS) to achieve a bacterial concentration of 1.8 mg/100 $\mu$l. One hundred $\mu$l were pipetted into a series of 12×75 mm polypropylene tubes for binding studies.

Antibodies

Several species and types of purified immunoglobulins were prepared and labelled with $^{125}$I employing a modification of the chloramine T method. Immunoglobulins were radiolabelled and average specific activity of the radiolabelled antibodies were: a) rabbit anti-CG (26 $\mu$Ci/$\mu$g); b) rabbit anti goat immunoglobulin (30 $\mu$Ci/$\mu$g); c) mouse monoclonal anti CG (16 $\mu$Ci/ug); d) mouse monoclonal anti alpha CG (24 $\mu$Ci/$\mu$g); and e) FC of human IgG (38 $\mu$Ci/$\mu$g). Polyclonal rabbit anti CG and rabbit-anti goat immunoglobulin were purified by Staphylococcus Protein A chromatography. The monoclonal mouse anti alpha-CG, and anti CG were also purified by Protein A chromatography. Fc of human IgG, F(ab$^1$)$_2$ fragments of human IgG and human IgG$_1$, IgG$_2$, IgG$^3$, IgG$^4$, were purchased from Chemicon (El Segundo, Calif.). The IgG$_1$, IgG$_2$, IgG$^3$, and IgG$^4$ are listed as ≈95% pure.

The Fc fragment is reported to give a single band by immunoelectrophoresis. However, to ascertain whether various human IgG subclasses were contaminated with small amounts of human IgA, as these subclasses were purified from serum, 12% polyacrylamide gels were run with these human immunoglobulin subclasses, and stained them with Coomassie Blue R-250. A second gel was Western blotted onto nitrocellulose and hybridized with $^{125}$I-mouse antihuman IgG (Fc specific) antibodies purchased from Chemicon, El Segundo, Calif., and also with $^{125}$I-mouse anti-human IgA antibodies. The blots were autoradiographed at −700 C using a Kodak x-ray film for four days. No contamination of human IgG subclasses with human IgA was observed.

Myeloma cell lines TIB194/2F.11.15 producing murine monoclonal IgA antibody to trinitrophenol were purchased from the American Type Culture Collection, Rockville, Md. Cell lines were grown in RPMI medium 1640 with 10% fetal calf serum. The immunoglobulins were separated from fetal calf serum by Protein A chromatography.

To ascertain whether the calf serum were free of immunoglobulins, aliquots of Protein A purified calf serum were run on a 15% polyacrylamide gels, and subsequently transblotted onto nitrocellulose. The membrane was hybridized with $3 \times 10$ cpm/ml of $^{125}$I-mouse anti IgG antibody for 48 hours. The membranes were washed to remove unbound radioactivity and exposed to a Kodak x-ray film for two days. It was found that after four subsequent Protein A purification steps, the immunoglobulins present in calf serum were removed to a level not to be detected by the Western blot method. The monoclonal IgA produced by the myeloma cell lines was present in the media and was purified by Protein A chromatography. The yield of purified IgA was variable, yielding only about 20-30%.

Proteins A and G

*Staphylococcus aureus* Protein A was purchased from Sigma Chemical, St. Louis, Mo., and Streptococcal Protein G was purchased from Chemicon, El Segundo, Calif.

Whole Bacteria Binding Studies

One hundred $\mu$l containing 1.8 mg of whole bacteria (wet weight) were pipetted into a series of $12 \times 75$ mm polypropylene tubes. The $^{125}$I immunoglobulin being studied was pipetted into the tubes, along with varying amounts of unlabelled immunoglobulins, dissolved in 0.01M phosphate, 0.15M sodium chloride pH 7.4 buffer (PBS). The buffer in this and subsequent studies contained 0.15% BSA as a carrier protein. This percentage was selected by optimizing the assay using different percentages of BSA.

The presence of BSA decreased non-specific binding. Total volume in each tube was 1 ml. After 18-hour incubation, the tubes were centrifuged at 4000 RPM for 30 minutes. The supernatant was discarded and the pellet washed twice with PBS, 0.15% BSA. The radioactivity in the pellet was quantified in a gammaspectrometer. In some studies, the weights of the whole bacteria were varied.

Sonicated Preparation of Bacteria

Approximately 4 gms of a fresh batch of *Pseudomonas maltophilia* were suspended in 6 volumes of PBS. This preparation was subjected to sonication in a Bransonic sonicator for a period of 1 hour at room temperature, after which the preparation was centrifuged at 4000 RPM for 10 minutes and the supernatant retained for binding studies. The period of sonication was optimized for 1 hour because sonication beyond a period of 60-80 minutes resulted in decrease and ultimately loss of activity of the protein.

Binding Studies With The Sonicated Preparation

The protein concentration of the supernatant fluid from the sonicate was determined by known techniques. The sonicate was studied by incubation with various $^{125}$I-labelled and unlabelled immunoglobulins, such as Fc of IgG (10 $\mu$g), rabbit anti CG (100 $\mu$g), mouse anti CG #9 (10 $\mu$g), mouse anti alpha hCG (10 $\mu$g), rabbit anti goat IgG (10 $\mu$g).

In another set of experiments the sonicate was incubated with unlabelled IgA (10 $\mu$g), F(ab$^1$)$_2$ of IgG (10$\mu$g), IgG$_1$ (5 $\mu$g), IgG$_2$ (5 $\mu$g), IgG$_3$ (6 $\mu$g), IgG$_4$ (5 $\mu$g). Briefly, 1 $\mu$g of the sonicate supernatant was pipetted into $12 \times 75$ mm polypropylene tubes. The radiolabelled immunoglobulin probe to be tested along with the respective unlabelled antibody was added to it. The final volume of 1 ml was obtained by adding PBS and 0.15% BSA. After an 18 hour incubation at room temperature, the tubes were centrifuged at $10,000 \times g$ for 30 minutes. The supernatant was discarded and the pellet washed once with PBS. The radioactivity of the pellet was determined by a gammaspectrometer.

Binding/kinetic Studies Using Partially Purified Protein

Fifty mgs of the sonicate supernate in 5 ml PBS were subjected to Sephacryl S-300 column chromatography, 45 cm $\times$ 2.5 cm with a flow rate of 55 ml/hr, pre-equilibrated with PBS, and 3.5 ml fractions were collected. The protein concentrations of each fraction were estimated by measuring the optical density at 280 nm by a UV spectrophotometer. The immunoglobulin binding property was determined by incubating 1 ml of each fraction with radioiodinated Fc portion of human IgG, in $12 \times 75$ mm polypropylene tubes. After 18 hour incubation at room temperature, the tubes were centrifuged at $10,000 \times g$ for 30 minutes. The supernatant was discarded and the pellets were counted for radioactivity in a gammaspectrometer with an efficiency of 70%.

The tubes exhibiting immunoglobulin binding were pooled and lyophilized overnight. The lyophilate was resuspended in PBS, and its protein concentration was again determined. This protein mixture was then passed through a Sephadex G-100 column with PBS, of length $105 \times 1$ cm and a flow rate of 18.5 ml/hr. Two ml fractions were collected and analyzed for protein concentration by determining optical density at 280 nm by a UV spectrophotometer. The immunoglobulin binding property was determined as described earlier. The tubes containing activity were pooled and lyophilized.

Using this partially purified preparation, binding/displacement studies were performed in a similar manner to that of the whole bacteria and sonicated proteins. The radiolabelled probe in this study was Fc of human IgG while displacement was studied by using highly purified unlabelled Fc of human IgG, F(ab$^1$)$_2$ of IgG, murine monoclonal IgA, and various immunoglobulin subclasses. After incubation for 18 hours, the tubes were centrifuged at $10,000 \times g$ and the supernatant aspirated. Cpm present in the pellet was assessed in a gammaspectrometer.

To compare the specificity of immunoglobulin binding with known immunoglobulin binding proteins, the above studies were repeated by using Staphylococcal Protein A, Streptococcal Protein G, and as negative controls, two non-immunoglobulin binding proteins, bovine serum albumin (BSA), (Fraction V-RIA grade, Sigma Chemical, St. Louis, Mo.), and human transferrin (Sigma Chemical, St. Louis, Mo.) were also used. Bound protein was separated from non-bound 125I-Fc of IgG by centrifugation at 10,000×g for 30 min.

The equilibrium constant of the Ig-binding protein was determined by known techniques, but with a slight variation. The pseudomonas Ig-binding protein was radioiodinated with 125I by the modified chloramine-T method described previously. The specific activity was about 16 uCi/ug. About 10 mg of human IgG was conjugated to 10 ml of Sepharose beads, yielding a concentration of 1 mg/ml of IgG:beads. Here 20,000 cpm of 125I-pseudomonas Ig-binding protein, 60 ul of Sepharose-IgG beads, and different concentrations (0.01-100 ug) of unlabelled pseudomonas Ig-binding protein were mixed. This final volume of 0.5 ml was adjusted by adding PBS, 0.15% BSA. First a time study was performed to determine the hours required to achieve 50% and 100% binding. The assay tubes were incubated for 18 hours at 370 C centrifuged, and the radioactivity in the beads counted. The bound and free concentrations were calculated. Results were plotted, and analyzed by the Scatchard method.

Page/Western Blot Studies

Twenty-five micrograms of the sonicated preparation, and the partially pure protein were electrophoresed on a 12% polyacrylamide gel. Samples were run under denaturing conditions, containing both SDS and mercaptoethanol. In addition, samples were boiled for 10 minutes before application. Following electrophoresis, the gel was stained with Coomassie Blue R-250. Samples containing the partially pure protein were electrophoresed on a 12% polyacrylamide gel, and transblotted onto nitrocellulose membranes. The membranes were hybridized for 24 hours with the following radioiodinated probes ($2 \times 10^5$ cpm/ml), Fc of IgG, F(ab)$_2$, murine monoclonal IgA, and various immunoglobulin subclasses, i.e., $IgG_1$, $IgG_2$, $IgG_3$, and $IgG_4$. After washing away the unbound radioactivity, the membranes were autoradiographed for 4-8 hrs at $-700$ C by using a Kodak x-ray film on an image intensifier.

The kinetics of IgG-pseudomonas Ig-binding protein was analyzed using human IgG coupled to Sepharose. Initial time studies showed that the binding is slow, reaching 50% after nearly 10 hours. From here the binding was even slower, saturating at 18-20 hours. This interaction was studied at 40 C° and 370 C°, using human IgG. The binding at 40 C° greatly decreased, taking nearly 18 hours to achieve 50%.

Table 1 compares the equilibrium constants of the pseudomonas Ig-binding protein with that of Protein A and Protein G. As the equilibrium constant (Ka) of the reaction is equal to the absolute value of the slope of the curve, two distinct types of Ig-binding proteins were found to be present in pseudomonas. One has a very high affinity (Ka=$1.545 \times 101°$) and one with a low affinity (Ka =$2.36 \times 108$). As seen in Table 1, one type of the pseudomonas Ig-binding protein has an equilibrium constant in the same magnitude as that of Protein A and Protein G. There also exists a binding protein on pseudomonas of very low affinity. The preponderance of which may explain the length of time (10 hours) required to achieve 50% saturation as compared to Protein A, Protein G.

TABLE 1

| EQUILIBRIUM CONSTANTS OF VARIOUS PROTEINS USING HUMAN IgG | |
|---|---|
| | Equilibrium Constant (Human IgG) |
| Protein A | $6.7 \times 10^{-10}$ |
| Protein G | $4.4 \times 10^{-10}$ |
| Psuedomonal Protein | $1.54 \times 10^{-10} / 2.36 \times 10^{-8}$ |

Figure 3:
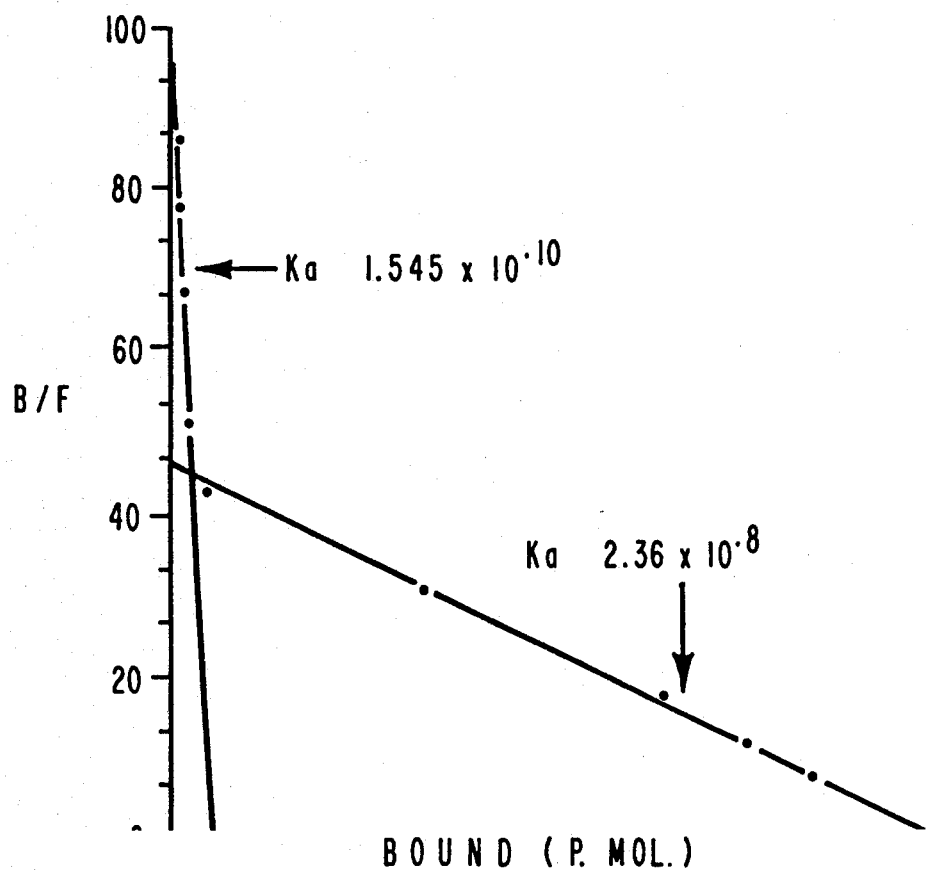
FIG. 3 illustrates a Scatchard plot for the reaction between the Pseudomonas Ig-binding protein and human IgG coupled to Sepharose beads.

FIG. 3 shows the Scatchard diagram of the Ig-binding protein, using human IgG coupled to Sepharose and radiolabelling the pseudomonas Ig-binding protein. Here two slopes were obtained: one having a high affinity (Ka=$1.545 \times 101°$) and one with a low affinity (Ka=$2.36 \times 108$).

The present invention shows that *Pseudomonas maltophilia* also has an immunoaccessible surface protein which binds IgG via their Fc regions, murine monoclonal IgA, but not F(ab)2 of IgG. This Scatchard analysis showed that there are two types of the protein, one with high affinity (Ka=$1.545 \times 101°$ and one with low affinity (Ka=$2.36 \times 10-8$), when using human IgG. The low affinity may exist in much larger quantity, thus explaining the 20 hour period of incubation required to attain saturation of binding to IgG-Sepharose.

EXAMPLES

The following examples are given to illustrate various embodiments which have been practiced or which may be practiced in accordance with the present invention. These examples are given by way of example only, and it is to be understood that the following examples are not comprehensive or exhaustive of the many types of embodiments of the present invention which can be practiced in accordance with the present invention.

EXAMPLE 1

In this example the procedures outlined above in the Experimental Techniques section were employed and are incorporated herein by this reference.

In FIG. 1 are shown the binding and competitive displacement of labelled rabbit, and mouse antibodies and of labelled Fc of IgG.

In this Example, bacteria bound $^{125}I$ immunoglobulin from three species in this system (cpm bound increased as the amount of $^{125}I$ immunoglobulin was increased). The percent of labelled immunoglobulin bound increased as the amount of bacteria added was increased. The $^{125}I$ immunoglobulin was competitively displaced not only by the same unlabelled immunoglobulin as was labelled, but also by unlabelled immunoglobulin from a different species. This binding and displacement did not relate to the antigenic determinants recognized by the immunoglobulins, but only to the fact that they were immunoglobulins. Thus, both rabbit anti CG and rabbit anti goat immunoglobulin bound and were competitively displaced. Similarly, both mouse monoclonal anti CG and anti alpha glycoprotein subunit bound and were competitively displaced. The Fc portion of human IgG also bound and was competitively displaced. Unlabelled F(ab$^1$)$_2$ fragments did not show binding.

EXAMPLE 2

The procedures set forth in the Experimental Techniques section above are incorporated herein by this reference.

In this example, 1.8 mg of whole bacteria was incubated with the five $^{125}I$-radiolabelled antibodies described in the Experimental Techniques, in the presence of increasing amounts of the respective unlabelled immunoglobulin. The percent labelled immunoglobulin increased from an average of 8% to 15% when the amount of bacteria was doubled from 0.9 to 1.8 mg per tube. For all five antibodies (two mouse, two rabbit and the FC portion of human IgG), there was a dose response related competitive displacement of the $^{125}$I-labelled immunoglobulin or FC fragment. The amount of immunoglobulin producing maximal displacement of label varied as follows: human Fc$\gamma$=1.8 ug, rabbit-anti CG=1 ug, rabbit anti goat IgG=10 ug, mouse anti CG=10 ug.

EXAMPLE 3

Figure 2B:
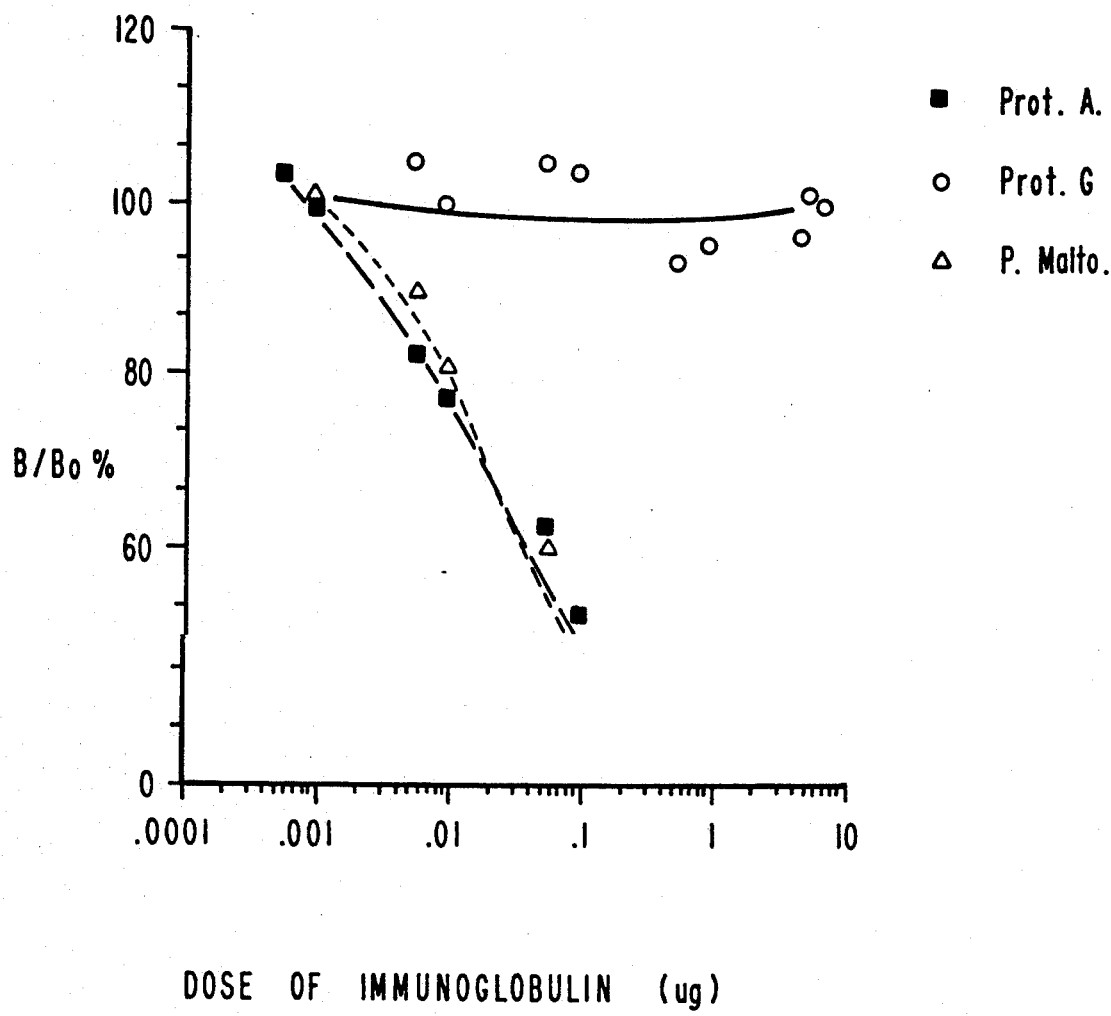
FIG. 2b is a dose response curve showing binding of $^{125}$I-Fc$\gamma$, with its competitive displacement by increasing doses of unlabelled murine monoclonal IgA.

A dose-response relationship was observed when the partially pure *Pseudomonas maltophilia* protein described above was incubated with $^{125}$I-Fc of human IgG, and increasing doses of unlabelled Fc of human F(ab$^1$)$_2$ of human IgG. Data concerning this Example is set forth in FIG. 2a. Similar dose-response relationships were also observed when Protein A of staphylococcus or Protein G of streptococcus was used as binding proteins.

For all the above studies the concentrations of Protein A, Protein G, and the pseudomonas protein were normalized by first performing titres to give 25-27% binding of $^{125}$I Fc. With two exceptions, all immunoglobulins competed for 125I-Fc binding in identical dose response relations for all three immunoglobulin binding proteins.

The control proteins, BSA and transferrin, showed no binding of labelled immunoglobulin (data not shown).

EXAMPLE 4

In this example the experimental technique of Example 3 was used except monoclonal IgA was substituted for F(ab$^1$)$_2$. This immunological fraction displace radiolabelled Fc. Data concerning this Example is set forth in FIG. 2b.

For Protein G, murine monoclonal IgA failed to compete for Fc binding. for pseudomonas protein, IgA inhibited Fc binding.

EXAMPLE 5

Figure 2C:
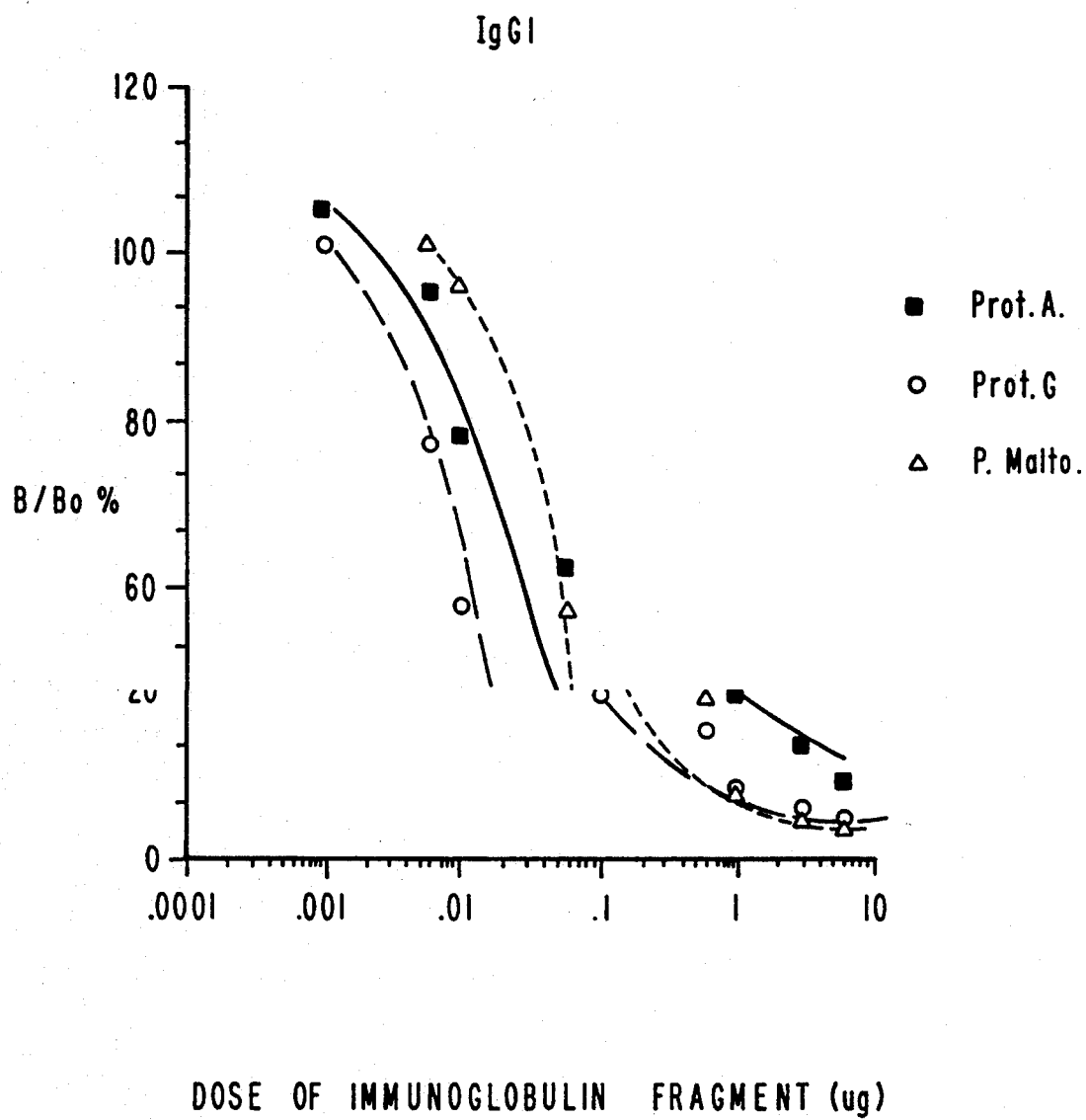
FIG. 2c is a dose response curve showing binding of $^{125}$I-Fc$\gamma$, with its competitive displacement by unlabelled human IgG$_1$.

In this example the experimental technique of Example 3 was used except human IgG$_1$ was substituted for F(ab$^1$)$_2$. This immunological fraction displace radiolabelled Fc. Data concerning this Example is set forth in FIG. 2c.

EXAMPLE 6

Figure 2D:
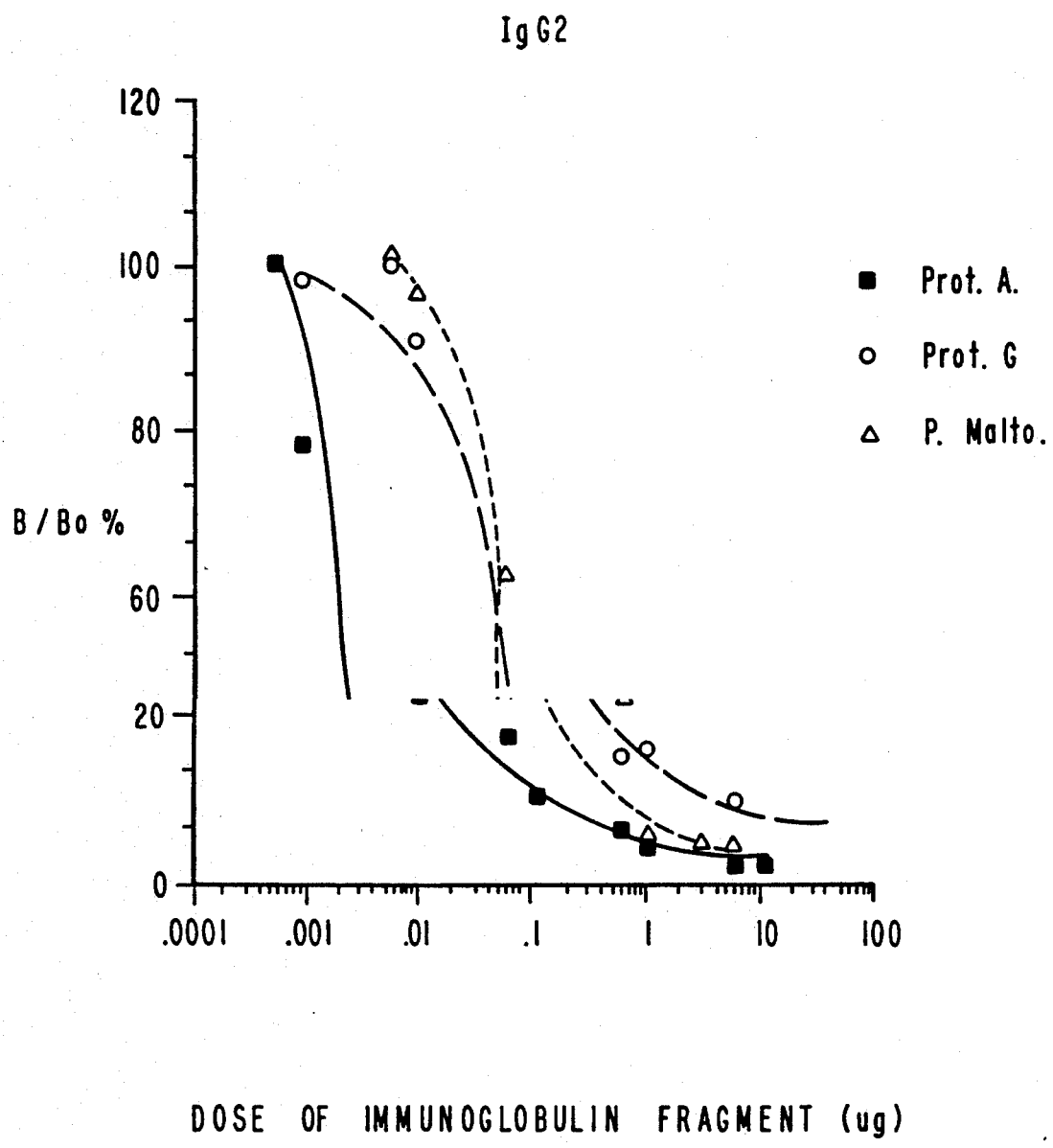
FIG. 2d is a dose response curve showing binding of $^{125}$I-Fc$\gamma$, with its competitive displacement by increasing doses of unlabelled human IgG$_2$.

In this example the experimental technique of Example 3 was used except human IgG$_2$ was substituted for F(ab$^1$)$_2$. This immunological fraction displace radiolabelled Fc. Data concerning this Example is set forth in FIG. 2d.

EXAMPLE 7

Figure 2E:
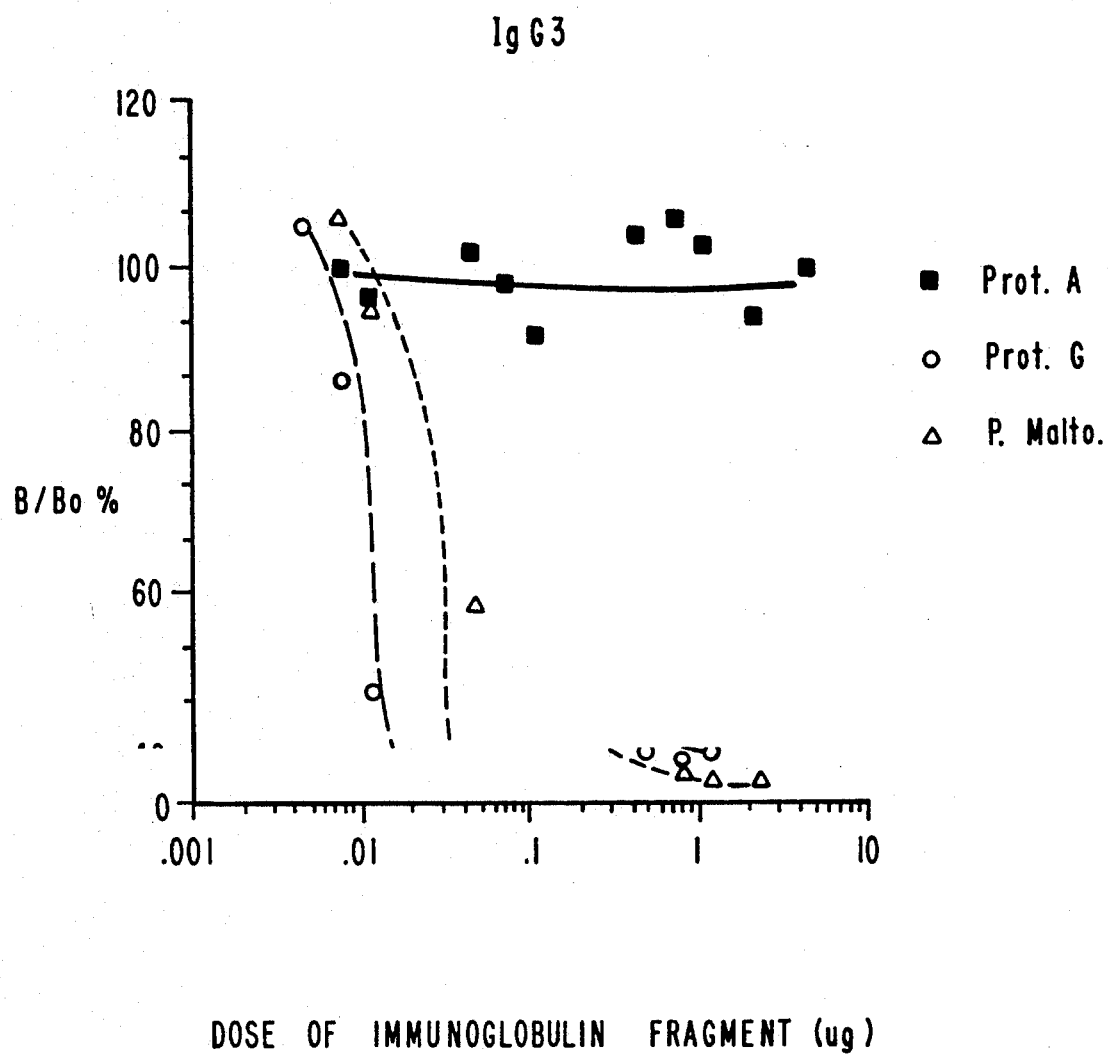
FIG. 2e is a dose response curve showing binding of $^{125}$I-Fc$\gamma$, with its competitive displacement by increasing doses of unlabelled human IgG$_3$.

In this example the experimental technique of Example 3 was used except human IgG$_3$ was substituted for F(ab$^1$)$_2$. This immunological fraction displace radiolabelled Fc. Data concerning this Example is set forth in FIG. 2e.

For Staphylococcal Protein A, IgG3 failed to compete for FC binding while for pseudomonas protein, IgG3 inhibited Fc binding.

EXAMPLE 8

Figure 2F:
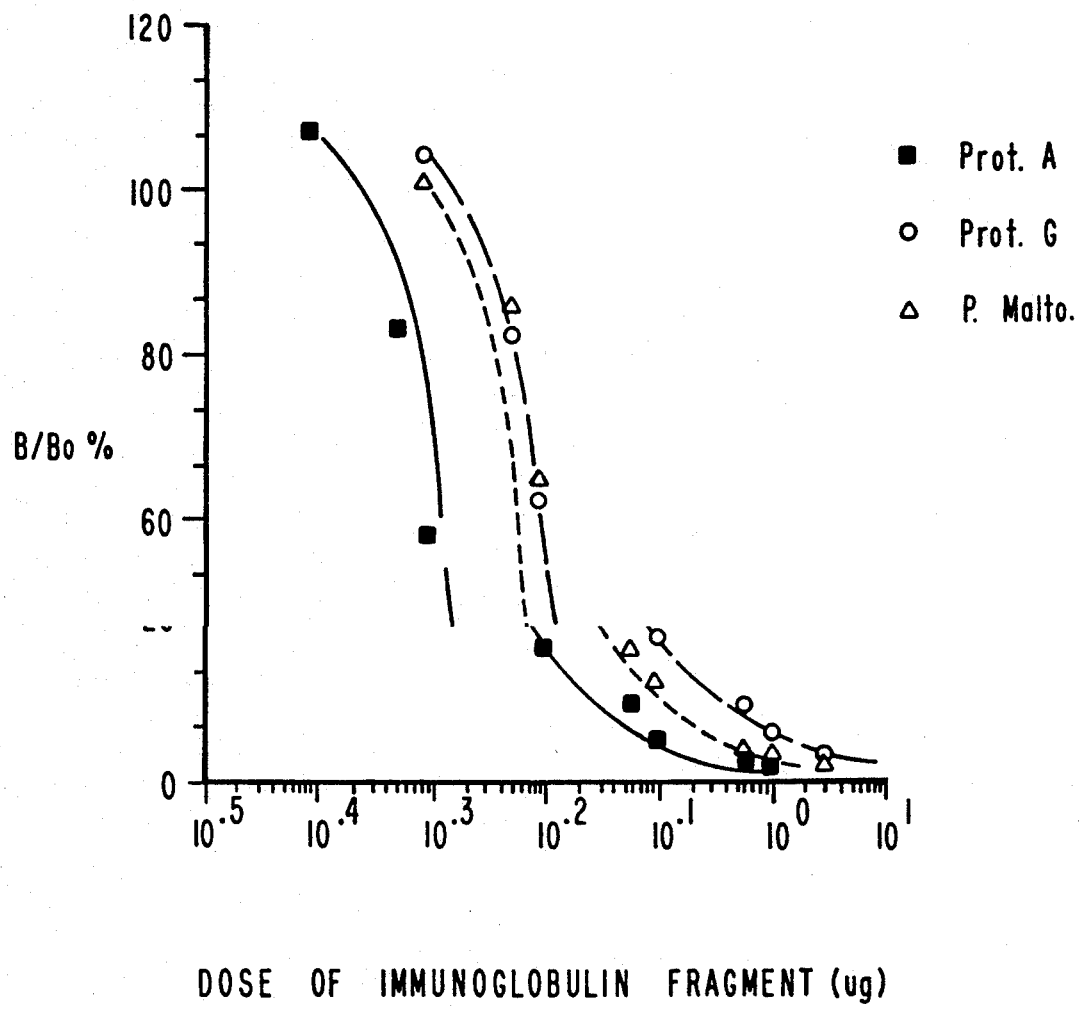
FIG. 2f is a dose response curve showing binding of $^{125}$I-Fc$\gamma$, with its competitive displacement by increasing doses of unlabelled human IgG$_4$.

In this example the experimental technique of Example 3 was used except human IgG4 was substituted for F(ab$^1$)$_2$. This immunological fraction displace radiolabelled Fc. Data concerning this Example is set forth in FIG. 2f.

EXAMPLE 9

The immunoglobulin binding protein obtained from *Pseudomonas maltophilia* was characterized using known techniques and techniques mentioned in the Experimental Techniques section above.

Figure 4A:
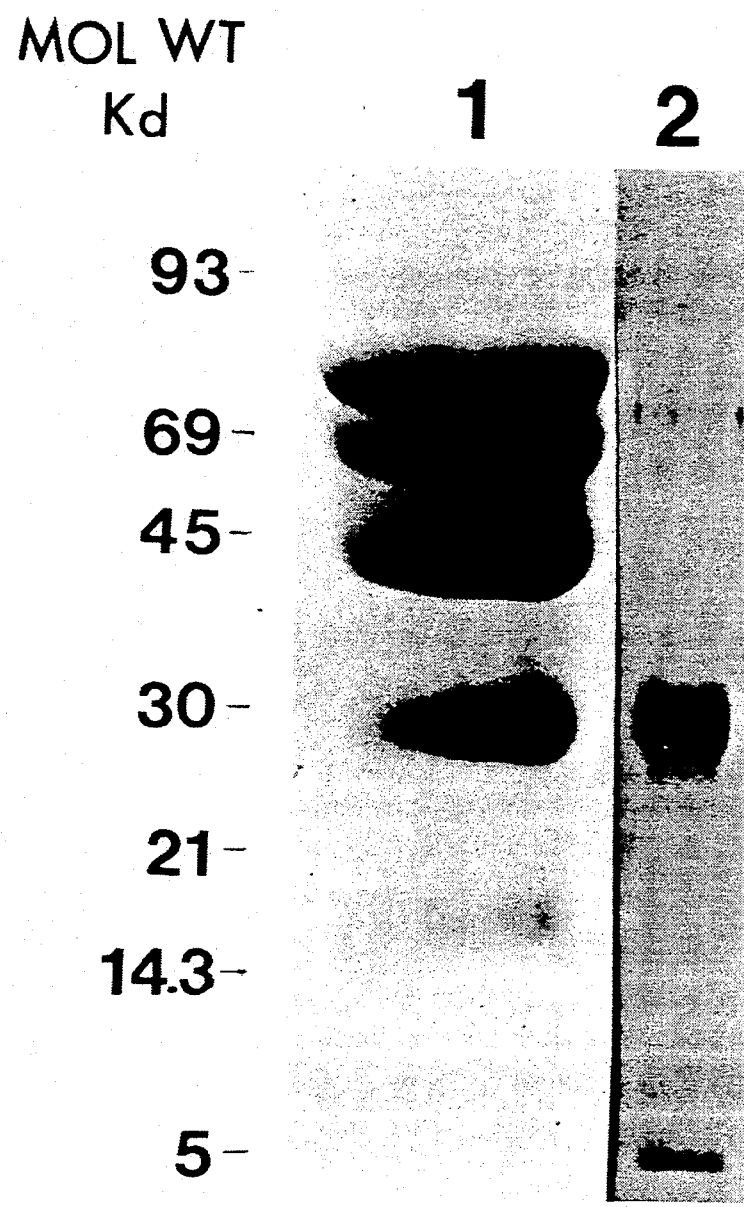
FIG. 4a illustrates the results of electrophoresis of purified protein on a 12% polyacrylamide gel.

FIG. 4a shows a 12% polyacrylamide gel stained with Coomassie Blue. Lane 1 shows the profile of the sonicated proteins. Lane 2 shows the profile of the purified preparation. These experiments showed that there is a major band at 30,000 daltons and there are also minor bands at 69,000 and 5,000 daltons.

Figure 4B:
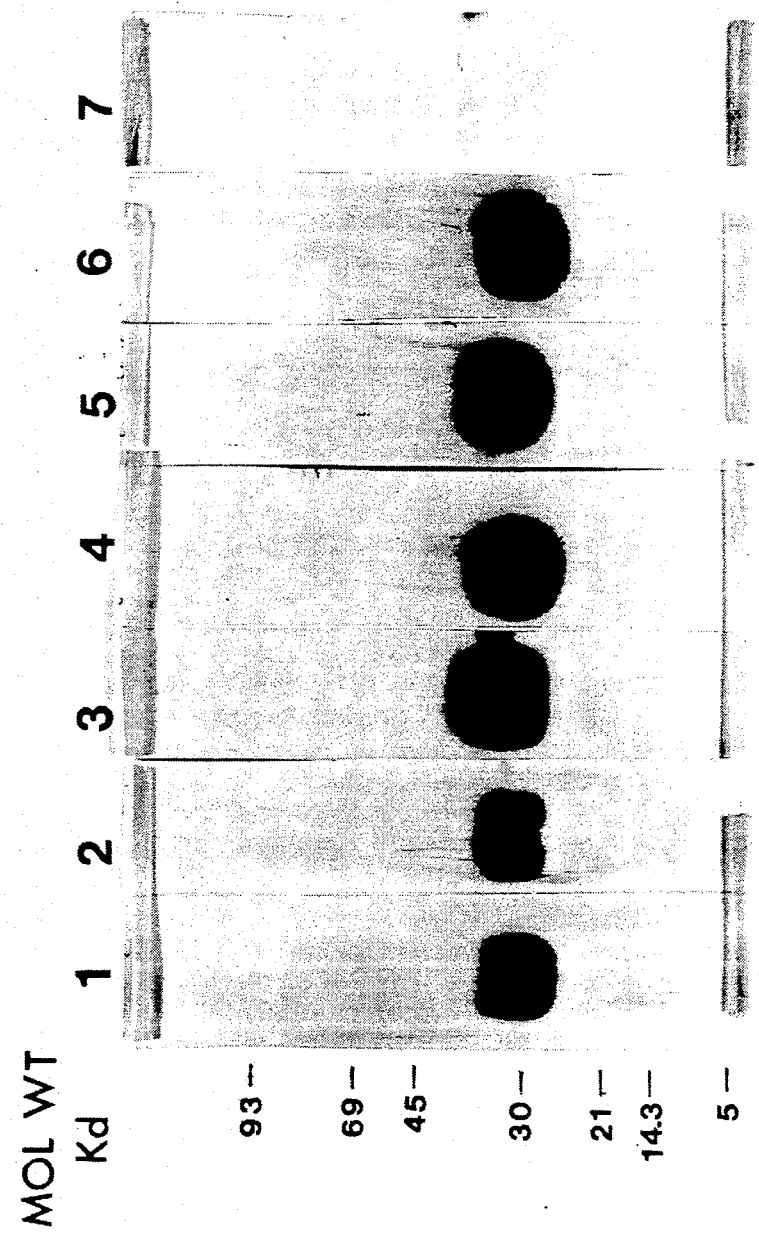
FIG. 4b illustrates the Western blot analysis of the purified Ig-binding protein hybridized with a number of immunoglobulins.

FIG. 4B shows Western blot analysis of the purified protein hybridized with various radiolabelled probes. As seen in FIG. 4b, Fc$\gamma$, murine monoclonal IgA, and various human immunoglobulin subclasses showed reaction towards the immobilized protein, whereas human F(a$^1$)$_2$ did not show any reaction. The major band identified in FIG. 4a Lane 2 was identified to be the immunoactive part at 30,000 daltons.

EXAMPLE 10

In this example, a biological sample containing a mixture of immunoglobulins and other materials is obtained. Such a sample originates from a source containing adequate quantities of immunoglobulins, including blood, gastrointestinal fluids, cells, or other secretions. Since such sample contains a mixture of immunoglobulins and other materials which are not of interest, it is necessary to separate the immunoglobulins from the mixture.

Separation of the immunoglobulins from the other fluid components is accomplished by contacting the fluid with an effective concentration of the immunoglobulin binding protein of the present invention. The protein binds both IgA and IgG within the biological fluid, and a mixture of immunoglobulins is recovered from the remainder of the materials present in the mixture. The recovered immunoglobulins are then separated into their component parts, including specifically IgA and IgG. The IgG immunoglobulins are removed by contacting with Protein G. Since Protein G fails to bind the IgA in the sample, only IgA remains.

EXAMPLE 11

In this example an IgA recovery procedure is run in a limited number of steps. A biological sample is obtained as disclosed in Example 10. The sample is initially contacted with Protein G. Since this protein binds IgG but not IgA, IgG will be removed from the sample. This leaves a sample containing only IgA immunoglobulins, along with the remainder of the sample which is comprised of material which is not of interest.

The *Pseudomonas maltophilia* protein of the present invention is then used to remove the remaining immunoglobulins from the sample. Those immunoglobulins will comprise only IgA, since the other immunoglobulins have been removed in the previous step. At this point in the process the IgA is separated from the *Pseudomonas maltophilia* protein, leaving a substantially pure IgA product.

In summary, the *Pseudomonas maltophilia* protein of the present invention differs in the spectrum of immunoglobulins bound from that of Staphylococcal Protein A in that it binds human IgG3, while Protein A does not bind IgG3. The pseudomonal immunoglobulin binding protein also differs from Protein G in that the former binds IgA while Protein G does not bind IgA. These properties suggest the three binding proteins are products of different genes.

The immunoglobulin binding protein of the present invention is also readily and easily used in the purification of IgA, thus avoiding the complex and expensive IgA isolation procedures presently in use.

The present invention also provides a simple and easily operable method for isolating IgA from a wide variety of biological fluids. The present invention provides a mechanism for separating bacteria containing IgA immunoglobulins from bacteria lacking IgA immunoglobulins. The present invention is also useful as a diagnostic and research means for quantifying IgA in disease mechanisms and in studying IgA-related illnesses.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A process for isolating IgA immunoglobulins from a biological sample comprising the steps of:
   a. obtaining a biological sample having as one of its components IgA immunoglobulins;
   b. contacting said biological sample with an effective quantity of immunoglobulin binding protein, or subfragments of said protein, said protein being capable of binding both IgG and IgA immunoglobulins and having an apparent molecular weight of approximately 30,000 daltons as measured by SDS-Page or Western blot;
   c. separating the binding protein and bound immunoglobulins from the biological sample;
   d. separating the binding protein from the bound immunoglobulins;
   e. contacting the separated immunoglobulins of step (d) with an IgG binding protein, such that essentially all of the IgG in the separated immunoglobulins is bound by the IgG binding protein; and
   f. removing the IgG and IgG binding protein from the remaining IgA.

2. A process for isolating IgA immunoglobulins from a biological sample as defined in claim 1 wherein the protein which is capable of binding both IgG and IgA immunoglobulins is isolated from the bacterium *Pseudomonas maltophilia*.

3. A process for isolating IgA immunoglobulins from a biological sample as defined in claim 5 wherein the IgG binding protein is selected from the group consisting of said protein having an apparent molecular weight of approximately 30,000 daltons as measured by SDS-Page or Western blot, Protein A, and Protein G.

4. A process for isolating IgA immunoglobulins from a biological sample as defined in claim 1 wherein the biological sample is selected from the group consisting of gastro-intestinal fluids, blood, cells, and bodily secretions.

5. A process for isolating IgA immunoglobulins comprising the steps of:
   a. obtaining a biological sample having as one of its components IgA immunoglobulins;
   b. contacting the biological sample with at least one IgG binding protein such that an IgG-IgG binding protein complex is formed;
   c. removing from said sample the resulting IgG-IgG binding protein complex;
   d. contacting the remainder of said biological sample with immunoglobulin binding protein, said protein being capable of binding both IgG and IgA immunoglobulins and having an effective molecular weight of approximately 30,000 daltons as measured by SDS-Page or Western blot;
   e. separating the binding protein and bound IgA immunoglobulins from the remainder of the biological sample;
   f. separating the binding protein from the bound IgA immunoglobulins.

6. A process for isolating IgA immunoglobulins as defined in claim 5 wherein said immunoglobulin binding protein is isolated from the bacterium *Pseudomonas maltophilia*.

7. A process for isolating IgA immunoglobulins as defined in claim 5 wherein said immunoglobulin binding protein comprises a protein isolated from the outer membrane envelope of Pseudomonas maltophilia ATCC 13637.

8. A method for isolating IgA immunoglobulins from a biological sample, comprising the steps of:
   a. preparing an array of IgA binding protein secured to a substrate, said IgA binding protein comprising a protein isolated from the cell wall of *Pseudomonas maltophilia* and having an effective molecular weight of 30,000 daltons as measured by SDS-Page or Western blot;
   b. contacting said sample with said array;
   c. separating the unbound material from the material bound to the binding protein; and
   d. separating the binding protein from the bound material.

9. A method for isolating IgA immunoglobulins as defined in claim 8 wherein said substrate comprises a gel.

10. A method for isolating IgA immunoglobulins as defined in claim 8 wherein said substrate comprises a column.

11. A method for isolating IgA immunoglobulins as defined in claim 8 wherein said biological sample comprises bacteria.

12. A method for isolating IgA immunoglobulins as defined in claim 8 wherein said biological sample comprises a mixture of species of bacteria.

13. A method for isolating IgA immunoglobulins as defined n claim 8 wherein the biological sample is selected from the group consisting of gastro-intestinal fluids, blood, cells, and bodily secretions.

14. A method for isolating IgA immunoglobulins as defined in claim 8 further comprising the step of identifying the bound material.

15. A process for isolating IgA immunoglobulins from a biological sample comprising the steps of:
   a. obtaining a biological sample having as one of its components IgA immunoglobulins;

b. contacting said biological sample with an immunoglobulin binding protein, or subfragments of said protein, said protein being capable of binding both IgG and IgA immunoglobulins and having an apparent molecular weight of approximately 30,000 daltons as measured by SDS-Page or Western blot;

c. separating the binding protein and bound immunoglobulins from the biological sample;

d. separating the binding protein from the bound immunoglobulins;

e. contacting the separated immunoglobulins of step (d) with a protein which binds IgG and IgM, but does not bind IgA, such that essentially all of the IgG and IgM in the mixture is bound by the protein; and f. removing the IgG, IgM, and the binding protein from the remaining IgA.

16. A process for isolating IgA immunoglobulins from a biological sample as defined in claim 15 wherein said protein which binds IgG and IgM, but does not bind IgA, comprises Protein G.

17. A process for isolating IgA immunoglobulins comprising the steps of:

a. obtaining a biological sample having as one of its components IgA immunoglobulins;

b. contacting the biological sample with at least one binding protein which binds IgG and IgM, but which does not bind IgA, such that IgG-binding protein and IgM-binding protein complexes are formed;

c. removing from said sample the resulting bound complexes;

d. contacting the remainder of said biological sample with an immunoglobulin binding protein, said protein being capable of binding both IgG and IgA immunoglobulins and having an effective molecular weight of approximately 30,000 daltons as measured by SDS-Page or Western blot;

e. separating the binding protein and bound IgA immunoglobulins from the biological sample; and d. separating the binding protein from the bound IgA immunoglobulins.

18. A process for isolating IgA immunoglobulins as defined in claim 17, wherein said protein which binds IgG and IgM, but does not bind IgA, comprises Protein G.

* * * * *